(12) United States Patent
Birkenbach et al.

(10) Patent No.: US 8,160,743 B2
(45) Date of Patent: Apr. 17, 2012

(54) ANTHROPOMORPHIC MEDICAL ROBOT ARM WITH MOVEMENT RESTRICTIONS

(75) Inventors: Rainer Birkenbach, Aufkirchen (DE); Andreas Hartlep, Naring (DE); Richard Wohlgemuth, München (DE); Michael Bertram, Markt Schwaben (DE); Alin Albu-Schäffer, München (DE); Markus Grebenstein, München (DE); Ulrich Hagn, Pähl (DE); Klaus Jöhl, Gilching (DE); Mathias Nickl, München (DE); Tobias Ortmaier, Germering (DE); Franz Hacker, Fuchstal (DE); Rainer Konietschke, Gilching (DE); Stefan Jörg, München (DE)

(73) Assignee: Brainlab AG, Feldkirchen (DE)

( * ) Notice: Subject to any disclaimer, the term of this patent is extended or adjusted under 35 U.S.C. 154(b) by 1158 days.

(21) Appl. No.: 11/464,940

(22) Filed: Aug. 16, 2006

(65) Prior Publication Data
US 2007/0129846 A1   Jun. 7, 2007

Related U.S. Application Data

(60) Provisional application No. 60/803,302, filed on May 26, 2006.

(30) Foreign Application Priority Data

Aug. 16, 2005  (EP) .................................. 050177252

(51) Int. Cl.
*G06F 19/00* (2006.01)
*B25J 1/00* (2006.01)
*B25J 3/00* (2006.01)
*B25J 19/00* (2006.01)
*H02P 23/00* (2006.01)

(52) U.S. Cl. ................ 700/245; 414/1; 606/30; 318/362
(58) Field of Classification Search .................. 318/362; 414/1; 606/1, 30; 700/240
See application file for complete search history.

(56) References Cited

U.S. PATENT DOCUMENTS 4,046,262 A * 9/1977 Vykukal et al. ................. 414/5
(Continued)

FOREIGN PATENT DOCUMENTS

EP   1296609   1/2005
(Continued)

OTHER PUBLICATIONS

U. Hagn, "Development of a generic, force-reflecting manual controller for difference scenarios in medical technology", 2003, Bavarian network of authorities in mechatronics.

(Continued)

*Primary Examiner* — Khoi Tran
*Assistant Examiner* — Bao Long T Nguyen
(74) *Attorney, Agent, or Firm* — Renner, Otto, Boisselle & Sklar, LLP

(57) ABSTRACT

An anthropomorphic medical robot arm includes a base end, a first arm element, a base joint coupling the base end to the first arm element, a second arm element, a middle joint coupling the second arm element to the first arm element, a distal functional end, a distal joint coupling the distal functional end to the second arm element, and at least one selectively operable movement inhibitor operable on the base joint, middle joint and/or distal joint so as to restrict the functionally possible range of movement of the robot arm to the range of movement of a human arm.

18 Claims, 1 Drawing Sheet

U.S. PATENT DOCUMENTS

| | | | |
|---|---|---|---|
| 4,260,940 A * | 4/1981 | Engelberger et al. | 318/562 |
| 4,550,383 A * | 10/1985 | Sugimoto | 700/262 |
| 4,828,453 A | 5/1989 | Martin et al. | |
| 4,911,033 A | 3/1990 | Rosheim et al. | |
| 4,986,723 A * | 1/1991 | Maeda | 414/729 |
| 5,791,231 A | 8/1998 | Cohn et al. | |
| 5,923,139 A * | 7/1999 | Colgate et al. | 318/566 |
| 6,451,027 B1 | 9/2002 | Cooper et al. | |
| 6,642,686 B1 * | 11/2003 | Ruch | 318/568.21 |
| 6,741,911 B2 * | 5/2004 | Simmons | 700/245 |
| 6,788,018 B1 * | 9/2004 | Blumenkranz | 318/568.11 |
| 2001/0013764 A1 | 8/2001 | Blumenkranz et al. | |
| 2002/0050183 A1 | 5/2002 | Takenaka et al. | |
| 2004/0116906 A1 * | 6/2004 | Lipow | 606/1 |
| 2005/0075757 A1 * | 4/2005 | Haas et al. | 700/245 |
| 2009/0183740 A1 * | 7/2009 | Sheffer et al. | 128/882 |
| 2010/0043610 A1 * | 2/2010 | Tanaka | 83/22 |

FOREIGN PATENT DOCUMENTS

| | | |
|---|---|---|
| JP | 9190207 | 7/1997 |
| WO | 2003/077101 | 9/2003 |

OTHER PUBLICATIONS

T. Ortmaier et al., "Design requirements for a new robot for minimally invasive surgery", Nov. 2004, An International Journal, Special Edition on Medical Robotics, 31(6), pp. 493-498.

Barrett Technology Inc., WAM Arm Data Sheet, http://www.barrett.com, 10 pages.

* cited by examiner

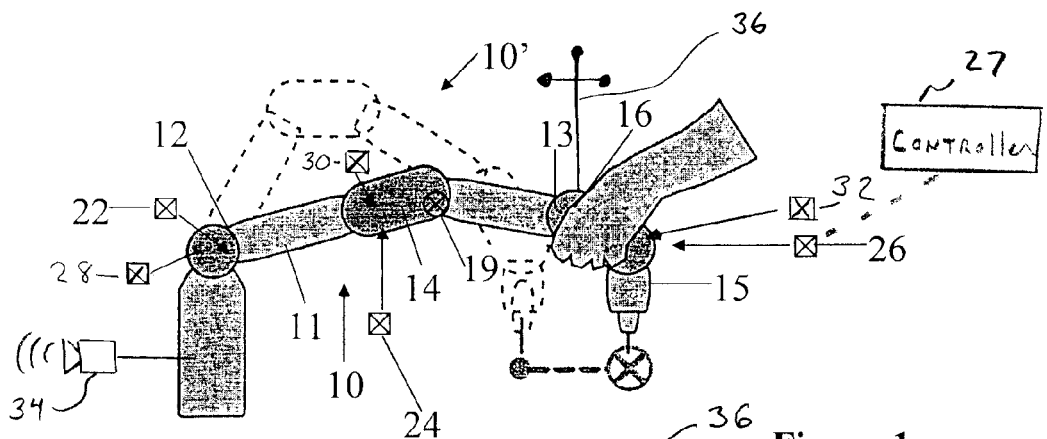
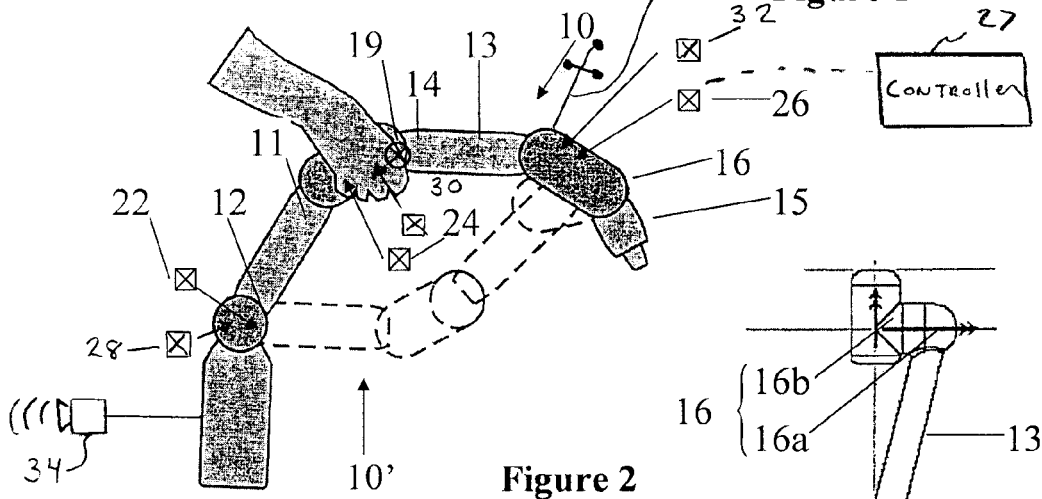
Figure 1
Figure 2
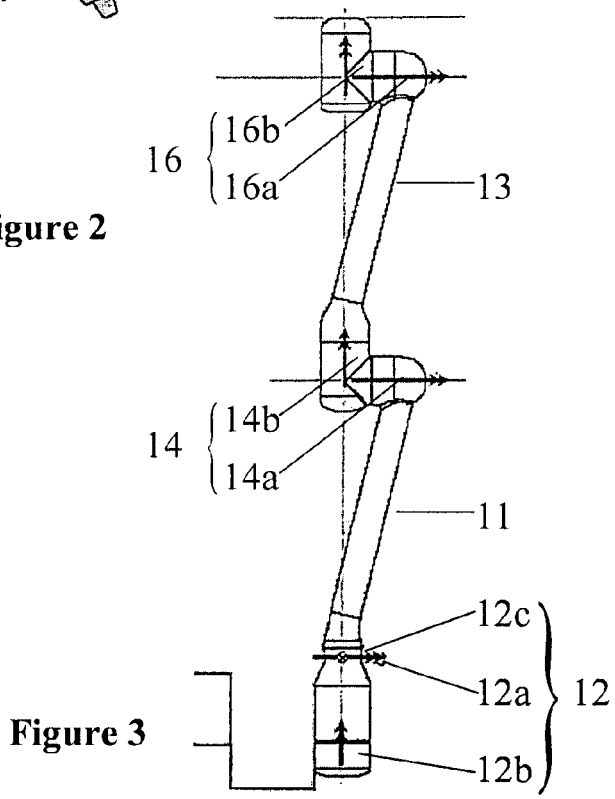
Figure 3

ANTHROPOMORPHIC MEDICAL ROBOT ARM WITH MOVEMENT RESTRICTIONS

RELATED APPLICATION DATA

This application claims priority of U.S. Provisional Application No. 60/803,302 filed on May 26, 2006, and European Patent Application No. 05017752.6 filed on Aug. 16, 2005, each of which is incorporated by reference in its entirety.

FIELD OF THE INVENTION

The present invention relates to an anthropomorphic medical robot arm and to a method for operating such a robot arm.

BACKGROUND OF THE INVENTION

Anthropomorphic medical robot arms, for example, serve to assist in particular actions in a medical setting. They can be used to position or manipulate surgical tools such as, for example, endoscopes, biopsy needles, drills or implants. Existing robot systems are either remote-controlled (for example by a remote control input device) or directly manipulated and work partially or completely autonomously.

The company of Barrett Technology Inc., Cambridge, Mass., USA offers a robot arm for use in image-guided surgery and for many other applications under the name "WAM". This mobile arm, which includes a kinematic chain consisting of a shoulder joint, an elbow joint and a wrist joint, provides a haptic interaction with the user and, therefore, can be manually guided (see also www.barretttechnology.com).

JP 9-190207 proposes restricting the range of movement of the joint angles of a robot manipulator in order to avoid parts of the arm obstructing each other. The range of movement thus is only restricted enough that the overall functionally possible working range of the robot arm can be used, but movements outside this functionally possible range of movement are avoided.

EP 1 296 609 B1 describes a medical positioning device including at least three limbs, wherein joint axes of sequential joints are aligned perpendicularly and optimized such that an attached surgical tool can reach any target on the patient from almost any direction.

US 2002/0050183 A1 describes an anthropomorphic robot arm which is fastened to a torso and includes a structure that minimizes the occurrence of a state in which a small change at the elbow necessitates a large change at the shoulder position.

US 2001/0013764 A1 discloses a manipulator for aligning a surgical instrument with a treatment point, using a manual input control.

A method is known from WO 2003/077101 A3 in which the user of a surgical robot is provided with a haptic feedback, and the arm is positioned in response to an applied force. Using this method, the movement of the arm is restricted to defined trajectories or safety zones by a user guide.

The publication "Development of a generic, force-reflecting manual controller for different scenarios in medical technology" (U. Hagn, Project reports in the 2003 annual report of the Bavarian network of authorities in mechatronics) describes a surgical robot manipulator which can be guided by the user, wherein manipulation forces are measured and counter forces are applied.

The publication "Design requirements for a new robot for minimally invasive surgery" (T. Ortmaier, H. Weiss and V. Falk in: Industrial Robotics: An International Journal, Special Edition on Medical Robotics, 31(6), pages 493 to 498, November 2004) describes a kinematically redundant, surgical robot arm having kinematics and a connection length that are optimized for required working spaces with different minimally invasive surgical activities and with respect to precision.

SUMMARY OF THE INVENTION

A robot arm is provided with movement inhibitors that act on the joints and restrict the functional working range of the robot arm to the possible range of movement of a human arm by inhibiting the freedom of movement of the joints. The base joint can work like a ball joint having the freedom of movement of a human shoulder joint, the middle joint can work like hinges having a similar freedom of movement to a human elbow, and the distal joint again can work like two orthogonal hinges having a similar freedom of movement to a human wrist (the elbow and wrist can be designed identically as flexing-rolling joints). In other words, the robot arm invention can be restricted in its freedom of movement, such that it moves like a human arm, e.g., the robot arm does not use its overall functionally possible range of movement.

The phrase "functionally possible range of movement" as used herein refers to the range of movement that could logically be used by the robot arm, without the arm getting in its own way or obstructing itself and without limbs hitting each other. As described herein, this overall, functionally or logically possible working range of the robot arm can be restricted to the possible range of movement of a human arm, whereby the limits on the range of motion of the robot arm mimic the limits of the range of motion of the human arm This is advantageous, for example, in that the movements of an arm controlled in this manner or guided by hand become predictable and intuitively comprehensible to the user.

By contrast, existing robot arms, which utilize the overall functionally possible and logical working range, allow movements that are not intuitively comprehensible or predictable. On the one hand, this can lead to the user being surprised by the movement of the robot and, in the worst case scenario, to the robot colliding with treatment staff or treatment devices, unpredictably and unavoidably. A user of a robot arm as described herein will intuitively know what movement the robot could perform next, since such movements may be known based on the user's own arm. This improved, intuitive use shortens the learning time for operating the device and increases safety. The movement restrictions allow a surgical setting to be designed in which space is limited, in a similar or even identical way to a design for a conventional procedure performed by hand. Despite the movement restrictions, the kinematics of the arm are suitable for all possible surgical applications, just like a human arm.

In other words, the invention achieves advantages, for example, by anthropomorphically configuring the arm guided by the user, by holding the arm and accordingly applying forces and moments (haptic interaction) in conjunction with particular movement restrictions on the arm. In addition, the arm can simultaneously be used as a haptic feedback device and so provide information for the user. Just like a human arm, the robot arm advantageously provides at least one redundant degree of freedom of movement. In order to improve intuitive use and to facilitate predicting movements of the first limb of the arm and the second limb of the arm, the movements can be restricted further. The most intuitive movement restriction is that which is comparable to the human arm. Since anatomy can vary from one person to the next, a typical (tolerance) range for the restriction can be selected or the range of different individual anatomies can be used.

The robot arm can comprise position, angle and/or torque sensors on its joints, the sensors being connected to the movement inhibitors or their controls. The arm also can comprise at least seven joint connections, wherein at least three are grouped in the base joint, at least two in the middle joint, and at least two in the distal joint. The robot arm can comprise a tool or instrument adaptor at the distal functional end, in particular behind the distal joint.

The movement inhibitors on or in the joints can comprise brakes or drive means. Such drive means, for example, can be electric motors or also force transfer means such as belts or gear wheels. The brakes or drive means can establish haptic feedback such as a counter force or forces. An on-switch and/or off-switch for the movement inhibitors can be provided and can in particular comprise one of the following devices:

- a mechanical switch for at least one of the joints;
- a software-controlled switch for at least one of the joints;
- a wire-controlled or wirelessly controlled switch for at least one of the joints.

By providing an on- or off-switch for the movement inhibitors, in particular by providing a switch for the middle joint, one or more of the joint connections, for example, can be released, e.g., a movement restriction can be removed. However, because a switch on the joint is operated by the user (e.g., the switch may be pressed or otherwise activated/deactivated, which can apply to all the joints), the movement restriction may be disabled under the complete control of the user.

In accordance with one embodiment, the arm can comprise a signal device or can be connected to a signal device that emits a visible, tangible or audible signal in the event of a prohibited deviation. It is also possible to arrange at least one marker array on the arm, the position of which can be located and tracked by a tracking and/or navigation system.

In a method of operating a robot arm, the functionally possible working range of the robot arm is restricted to the possible range of movement of a human arm, for example by inhibiting the freedom of movement of the joints. The corresponding advantages have already been described above. If, for example, a marker array arranged on the arm is positionally located and tracked by a medical tracking and/or navigation system, then the arm can be localized, in particular redundantly.

As already mentioned above, the movement of the arm can be controlled by eliminating a redundant degree of freedom of movement, in particular given at least one of the following conditions:

- the vertical and/or horizontal distance from the middle joint to the proximal end can be minimized or maximized;
- the holding of the arm can be energetically optimized; and
- the distance from the middle joint to the proximal end or to a point in the vicinity can remain constant.

In accordance with a preferred embodiment, a restriction of the possible range of movement or the transition to a restriction is triggered by: a status detected by means of software; holding the arm; a user input; or an interaction or action generated by the arm control system itself.

BRIEF DESCRIPTION OF THE DRAWINGS

The forgoing and other embodiments of the invention are hereinafter discussed with reference to the drawings.

FIGS. 1 and 2 illustrate an exemplary robot arm in different operating states in accordance with the invention.

FIG. 3 illustrates a schematic drawing of an exemplary design of the robot arm in accordance with the invention.

DETAILED DESCRIPTION

FIGS. 1 and 2 schematically show an exemplary robot arm 10 that sits on a base 10a. A first joint 12 belonging to the arm 10 (also referred to herein as the base joint or shoulder joint) is situated on the base 10a. As follows from the schematic drawing in FIG. 2, the base joint 12 includes a number of jointed connections or joint connections that are indicated as rotational axes. From FIG. 3, the base joint or shoulder joint 12 includes three axes or joint connections that are shown by arrows, wherein the arrow 12c is perpendicular to the plane of the drawing.

A first arm element 11, which could also be referred to as the "upper arm" of the robot arm 10, is attached via a joint above the shoulder joint 12. The first arm element 11 continues in a direction toward a distal end of the arm 10 and ends at joint 14, which includes two joint connections or rotational axes. In FIG. 3, these rotational axes are again shown by arrows which have been provided with the reference signs 14a and 14b. The middle joint 14 could also be referred to as the "elbow joint" or "elbow". A second arm element 13 (or "lower arm") extends from the elbow 14 to a distal joint 16, which also can be referred to as the "wrist joint". As again follows from FIG. 3, the wrist joint 16 also has two rotational axes 16a, 16b, corresponding to the rotational axes of the joint connections 14a, 14b of the elbow joint 14.

A flange (not explicitly shown) can be attached to the front of the wrist joint 16, wherein a tool can be fastened via the flange. In FIG. 1 and FIG. 2, for example, a drill 15 is shown as the tool.

Lightweight construction materials can be used to form one or more portions of the arm 10. The exemplary anthropomorphic robot arm 10 includes at least seven joint connections or rotational axes, of which at least three are grouped in the shoulder 12, at least two in the elbow 14, and at least two in the wrist 16.

The joints 12, 14 and 16 and, in particular, their individual joint connections 12a-c, 14a,b and 16a,b, can be provided with torque sensors and position sensors 28, 30, and 32. Via these sensors, the angular position and torque conditions in the individual joints and, thus, in principle also the position and orientation of the tool tip, can be detected at any time. To this end, the robot arm is calibrated (zero position) as applicable before use.

The movement inhibitors 22, 24, 26 for the shoulder joint 12, the elbow joint 14 and the wrist joint 16 are connected or otherwise attached to the joints so as to on the joints. These movement inhibitors, for example, can be brakes, drive means (servomotors, belts, gear wheels) or any device the restricts, blocks or otherwise can inhibit motion, wherein the movement inhibitors can be switched on and off. The individual movement inhibitors 22, 24, 26 can act not only on the joints 12, 14, 16 but also on their individual joint connections or rotational axes (a, b, c).

The movement inhibitors 22, 24, 26 can be switched on and off as a whole or individually, and can be controlled by a suitable controller 27 (for sake of clarity shown only connected to inhibitor 26) such that the arm obtains the possible range of movement of a human arm, wherein it is perfectly possible to establish and permit certain tolerance ranges, as is also the case with human arms. The arm 10 as a whole advantageously can have dimensions that are similar to those of a human arm or which are within a range of actually possible human arm sizes. Using the movement inhibitors 22, 24, 26 then results in a certain freedom of movement, in which the arm can be directly moved by the user (the hand shown) intervening (haptic interaction). Such a movement, for example, is shown in the transition from the dotted-line position 10' to the position 10 in FIG. 1.

The transition from the position 10' (dotted line) to the position 10 in FIG. 2 may cause movements which could not be reproduced by a human arm. The arm would then resist this movement with the aid of the movement inhibitors 22, 24 and 26 or would directly prevent such a movement (haptic feedback/establishing a counter force). Further, the arm 10 can comprise a signal device 34 or can be connected to a signal device that emits a visible, tangible or audible signal in the event of a prohibited deviation. It is also possible to arrange at least one marker array 36 on the arm 10, the position of which can be located and tracked by a tracking and/or navigation system.

In this case, it is possible for the user to operate the switching-off button 19 which is shown beneath the hand in FIG. 2 (dotted line). The user thus performs an override by deliberately releasing the movement of the arm 10 by activating (e.g., pressing) the button 19. When the button 19 is deactivated (e.g., released), the arm 10 again will only be able to move like a human arm. The button 19 can act on one or more joints or one or more joint connections.

Providing and operating the robot arm 10 with the options indicated above provides the user with an intuitively controllable appliance that is predictable in its behavior and easy to learn.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:
1. An anthropomorphic medical robot arm comprising
a base end;
a first arm element;
a base joint coupling the base end to the first arm element;
a second arm element;
a middle joint coupling serially end to end the second arm element to the first arm element;
a distal functional end;
a distal joint coupling the distal functional end serially end to end to the second arm element;
at least one selectively operable movement inhibitor operable on the base joint, middle joint and/or distal joint so as to restrict the functionally possible range of movement of the robot arm; and
further comprising an on and/or off switch that selectively enables and/or disables the movement inhibitors, said on and/or off switch including at least one of a mechanical switch, a software-controlled switch, or a wire-controlled or wirelessly controlled switch.

2. The robot arm according to claim 1, further comprising position, angle and/or torque sensors on at least one of the base, middle or distal joints, said sensors being connected to the movement inhibitors or controls of the movement inhibitors.

3. The robot arm according to claim 1, wherein the arm comprises at least seven joint connections, wherein three of the joint connections are grouped in the base joint, two joint connections are in the middle joint, and two joint connections are in the distal joint.

4. The robot arm according to claim 1, further comprising a tool or instrument adaptor at the distal functional end.

5. The robot arm according to claim 4, wherein the tool or instrument adapter is behind the distal joint.

6. The robot arm according to claim 1, wherein the movement inhibitors comprise brakes or drive means.

7. The robot arm according to claim 1, further comprising a signal device that emits a visible, tangible or audible signal in the event of a prohibited movement deviation.

8. The robot arm according to claim 1, wherein the arm has associated therewith at least one marker array that can be positionally located and tracked by a medical tracking and/or navigation system.

9. A method for operating an anthropomorphic medical robot arm including a base end, a first arm element, a base joint coupling the base end to the first arm element, a second arm element, a middle joint coupling serially end to end the second arm element to the first arm element, a distal functional end, a distal joint coupling the distal functional end serially end to end to the second arm element, and at least one selectively operable movement inhibitor operable on the base joint, middle joint and/or distal joint, comprising limiting a range of motion of at least one of the base, middle or distal joints by enabling or disabling the at least one movement inhibitor so as to restrict the functionally possible range of movement of the robot arm; and
wherein enabling or disabling includes switching on and/or off the at least one movement inhibitor via at least one of a mechanical switch, a software-controlled switch for at least one of the joints, or a wire-controlled or wirelessly controlled switch.

10. The method according to claim 9, further comprising detecting positions, angles and/or torques on the joints and taking the detected positions, angles and/or torques into account when restricting the movement or controlling the joints.

11. The method according to claim 9, wherein limiting a range of motion includes braking or driving the joints.

12. The method according to claim 9, wherein the arm comprises at least seven joint connections, wherein three of the joint connections are grouped in the base joint, two of the joint connections are in the middle joint, and two of the joint connections are in the distal joint, and wherein one joint connection is fixed to the middle joint and can be released by a switch.

13. The method according to claim 9, further comprising emitting a visible, tangible or audible signal in the event of a prohibited or undesired movement deviation.

14. The method according to claims 9, further comprising tracking, via a medical tracking and/or navigation system, a position and orientation of at least one marker array arranged on the arm so as to localize the arm.

15. The method according to claim 14, wherein tracking a position and orientation includes redundantly tracking the position and orientation.

16. The method according to claims 9, further comprising controlling the movement of the arm so as to eliminate a redundant degree of freedom of movement, given at least one of the following conditions:
   the vertical and/or horizontal distance from the middle joint to the proximal end is minimized or maximized;
   the holding of the arm is energetically optimized; and
   the distance from the middle joint to the proximal end or to a point in the vicinity remains constant.

17. The method according to claim 9, wherein limiting a range of motion includes triggering the range on at least one of a status detected by software, holding the arm, a user input, or an interaction or action generated by the arm control system itself.

18. A computer program embodied on a non-transitory computer readable medium including computer executable instructions for controlling an anthropomorphic medical robot arm including a base end, a first arm element, a base joint coupling the base end to the first arm element, a second arm element, a middle joint coupling serially end to end the second arm element to the first arm element, a distal functional end, a distal joint coupling the distal functional end serially end to end to the second arm element, and at least one selectively operable movement inhibitor operable on the base joint, middle joint and/or distal joint, the computer executable instructions comprising code that causes a processor to limit a range of motion of at least one of the base, middle or distal joints by enabling or disabling the at least one movement inhibitor so as to restrict the functionally possible range of movement of the robot; and
   wherein enabling or disabling includes switching on and/or off the at least one movement inhibitor via at least one of a mechanical switch, a software-controlled switch for at least one of the joints, or a wire-controlled or wirelessly controlled switch.

* * * * *

UNITED STATES PATENT AND TRADEMARK OFFICE
CERTIFICATE OF CORRECTION

PATENT NO. : 8,160,743 B2  Page 1 of 1
APPLICATION NO. : 11/464940
DATED : April 17, 2012
INVENTOR(S) : Rainer Birkenbach et al.

It is certified that error appears in the above-identified patent and that said Letters Patent is hereby corrected as shown below:

Cover Page: item (73) Assignee: "Brainlab AG, Feldkirchen (DE)" should read – "Brainlab AG, Feldkirchen (DE) and Deutsches Zentrum für Luft- und Raumfahrt e.V., Köln (DE)"

Signed and Sealed this
Eighteenth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,160,743 B2
APPLICATION NO. : 11/464940
DATED : April 17, 2012
INVENTOR(S) : Rainer Birkenbach et al.

It is certified that error appears in the above-identified patent and that said Letters Patent is hereby corrected as shown below:

Title Page, Item (30):
"Foreign Application Priority Data
Aug. 16, 2005 (EP) ................................050177252" should read:
-- Foreign Application Priority Data
Aug. 16, 2005 (EP) ................................050177526 --

Signed and Sealed this
Fourteenth Day of May, 2013

Teresa Stanek Rea
*Acting Director of the United States Patent and Trademark Office*